United States Patent
Echarri et al.

(10) Patent No.: US 12,207,838 B2
(45) Date of Patent: Jan. 28, 2025

(54) CLOT RETRIEVER CLEANING FOR REINSERTION

(71) Applicant: DePuy Synthes Products, Inc., Raynham, MA (US)

(72) Inventors: Roberto Echarri, Miami, FL (US); Kirk Johnson, Weston, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 432 days.

(21) Appl. No.: 17/825,074

(22) Filed: May 26, 2022

(65) Prior Publication Data

US 2022/0280184 A1  Sep. 8, 2022

Related U.S. Application Data

(62) Division of application No. 16/508,452, filed on Jul. 11, 2019, now Pat. No. 11,395,675.

(51) Int. Cl.
| | | |
|---|---|---|
| *A61B 17/3207* | (2006.01) | |
| *A61L 2/18* | (2006.01) | |
| *A61B 17/22* | (2006.01) | |
| *A61B 17/32* | (2006.01) | |

(52) U.S. Cl.
CPC ........ *A61B 17/320758* (2013.01); *A61L 2/18* (2013.01); *A61B 2017/22035* (2013.01); *A61B 2017/320012* (2013.01); *A61L 2202/24* (2013.01)

(58) Field of Classification Search
CPC .. A61B 17/320758; A61B 2017/22035; A61B 2017/320012; A61B 2090/701; A61B 90/70; A61B 17/221; A61B 2017/22038; A61B 2017/22079; A61B 2017/22084; A61B 2017/22094; A61B 17/22; A61B 2217/007; A61L 2/18; A61L 2202/24; A61M 39/06; A61M 2025/0019; A61M 2025/0042; A61M 2039/0626
See application file for complete search history.

(56) References Cited

U.S. PATENT DOCUMENTS

| | | | |
|---|---|---|---|
| 4,288,882 A | 9/1981 | Takeuchi | |
| 6,391,037 B1 | 5/2002 | Greenhalgh | |
| 6,425,916 B1 | 7/2002 | Garrison et al. | |
| 9,232,992 B2 | 1/2016 | Heidner | |

(Continued)

FOREIGN PATENT DOCUMENTS

| | | |
|---|---|---|
| EP | 3 253 437 | 8/2016 |
| WO | 2018/093817 A1 | 5/2018 |

*Primary Examiner* — Ashley L Fishback
*Assistant Examiner* — Chima U Igboko
(74) *Attorney, Agent, or Firm* — Troutman Pepper Hamilton Sanders LLP

(57) ABSTRACT

A clot retrieval cleaning instrument can have bristles, fluid sprays, or other techniques to liberate captured clot material from a clot retrieval device so that it can be reinserted into a patient's vasculature for successive capture attempts. The cleaning instrument can be conveniently integrated or connected to a hemo stasis valve assembly so that the cleaning function can be performed without completely removing the clot retrieval device from the delivery system. Aspiration can be applied to remove the freed thrombus material. The cleaning instrument can be removable from the delivery system to facilitate the instrument's washing or disposal.

11 Claims, 7 Drawing Sheets

(56) References Cited

U.S. PATENT DOCUMENTS

| | | |
|---|---|---|
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka |
| 9,833,604 B2 | 12/2017 | Lam et al. |
| 9,833,625 B2 | 12/2017 | Waldhauser et al. |
| 10,478,322 B2 | 11/2019 | Bernard et al. |
| 2006/0064151 A1 | 3/2006 | Guterman |
| 2008/0281350 A1 | 11/2008 | Sepetka |
| 2010/0324649 A1 | 12/2010 | Mattsson |
| 2012/0283768 A1 | 11/2012 | Cox et al. |
| 2014/0135812 A1 | 5/2014 | Divino et al. |
| 2014/0200607 A1 | 7/2014 | Sepetka et al. |
| 2014/0371779 A1* | 12/2014 | Vale ............... A61B 17/221 606/200 |
| 2015/0374401 A1 | 12/2015 | Guggenheimer et al. |
| 2016/0067004 A1* | 3/2016 | Geddis ............... B08B 3/102 134/169 C |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0344427 A1 | 12/2018 | Rosenbaum et al. |

\* cited by examiner

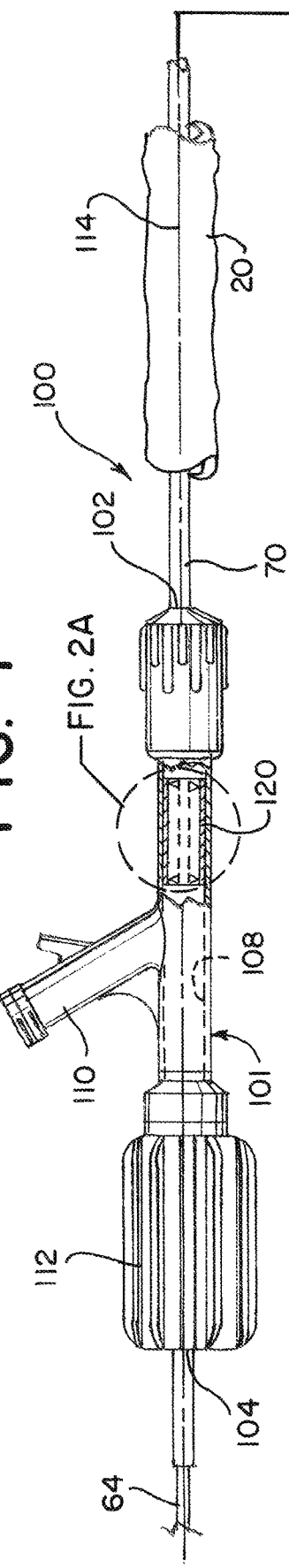
FIG. 1
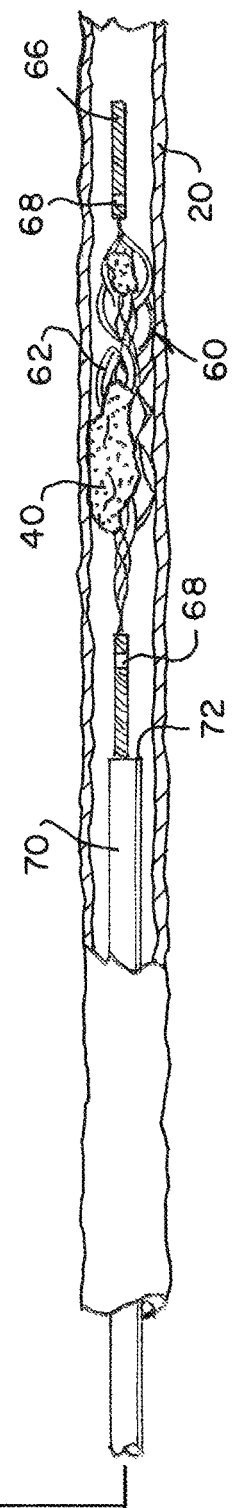
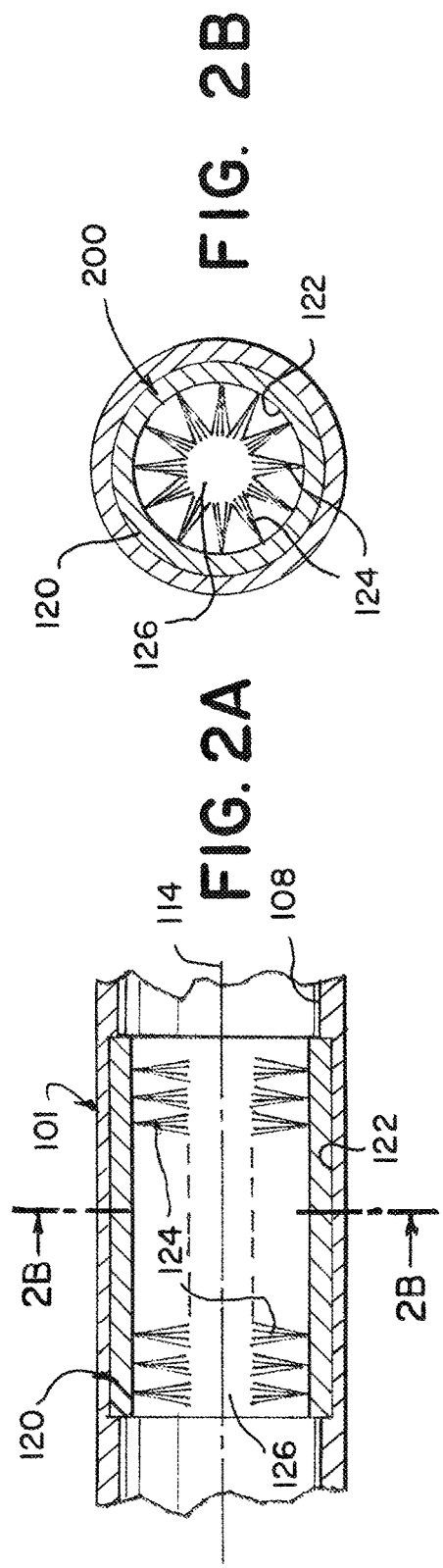
FIG. 2A
FIG. 2B

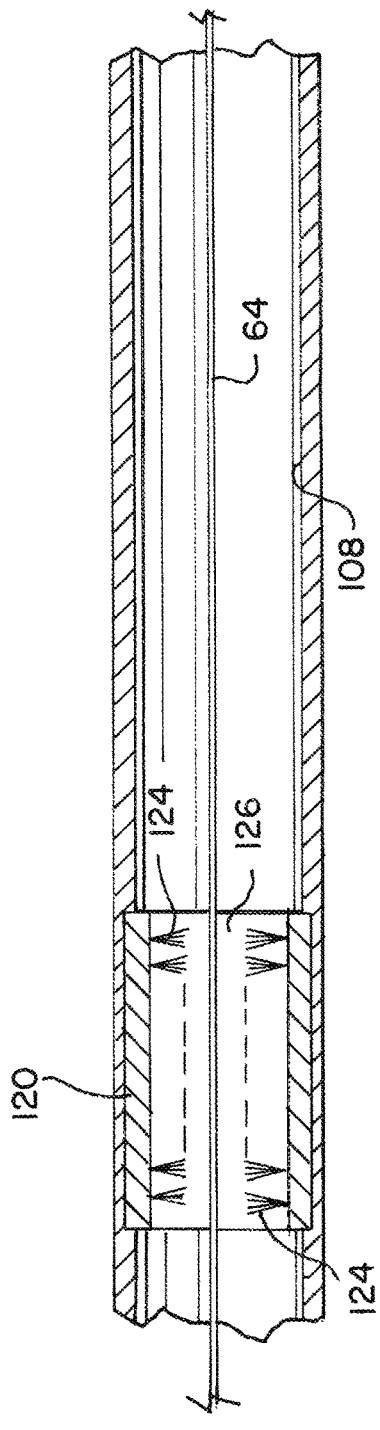
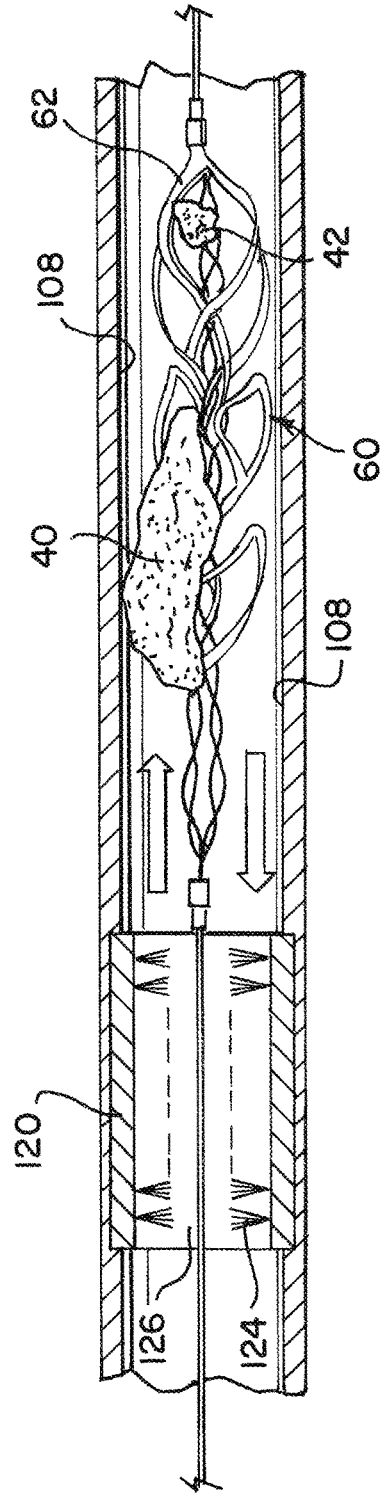
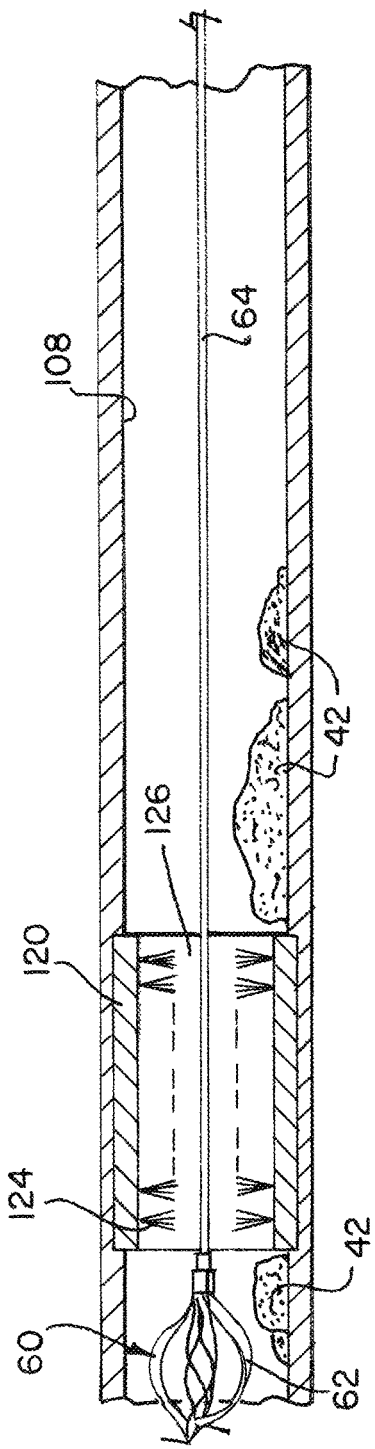

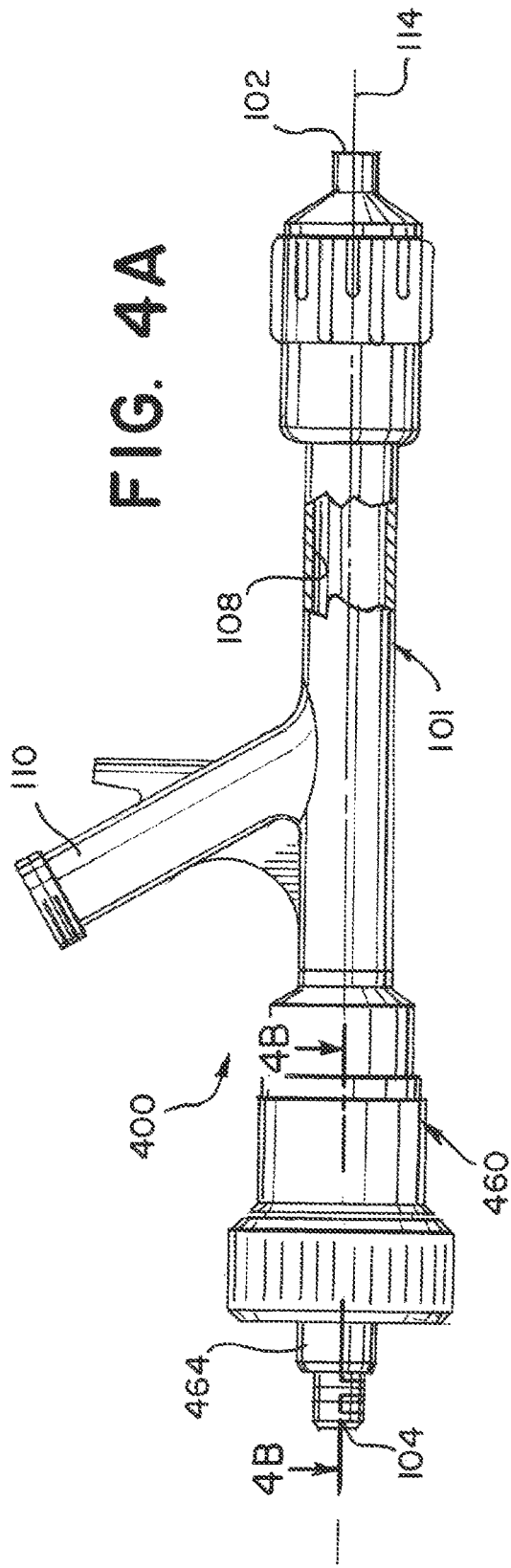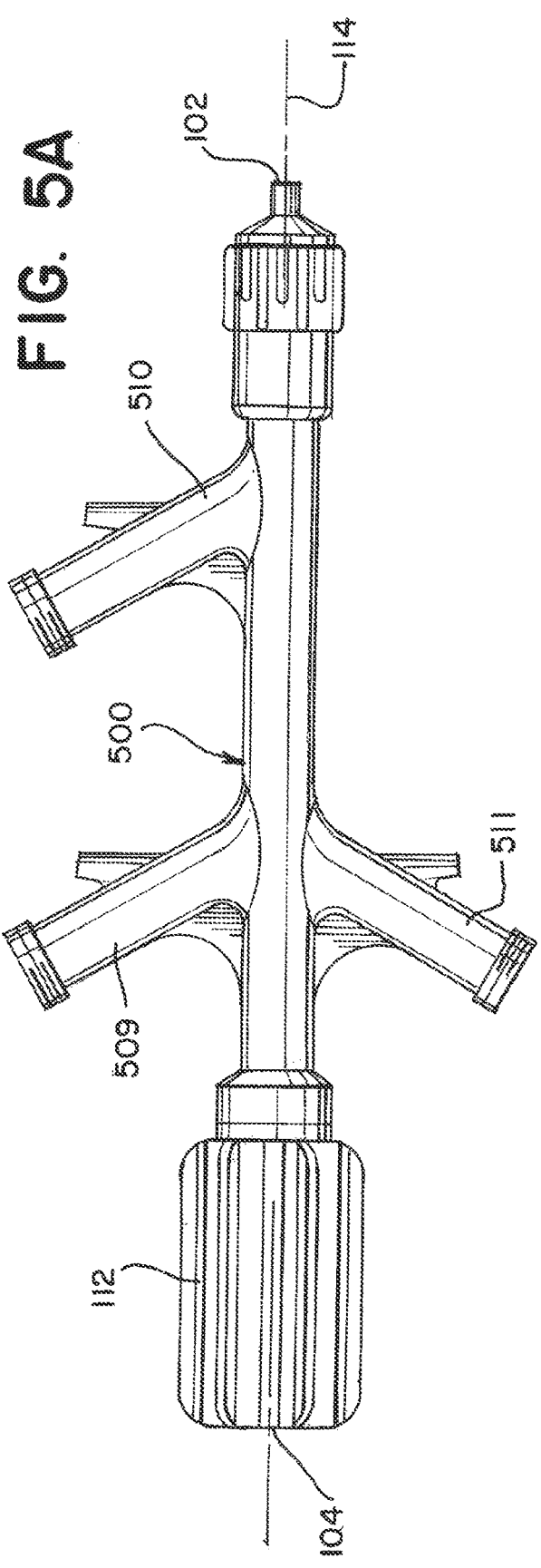

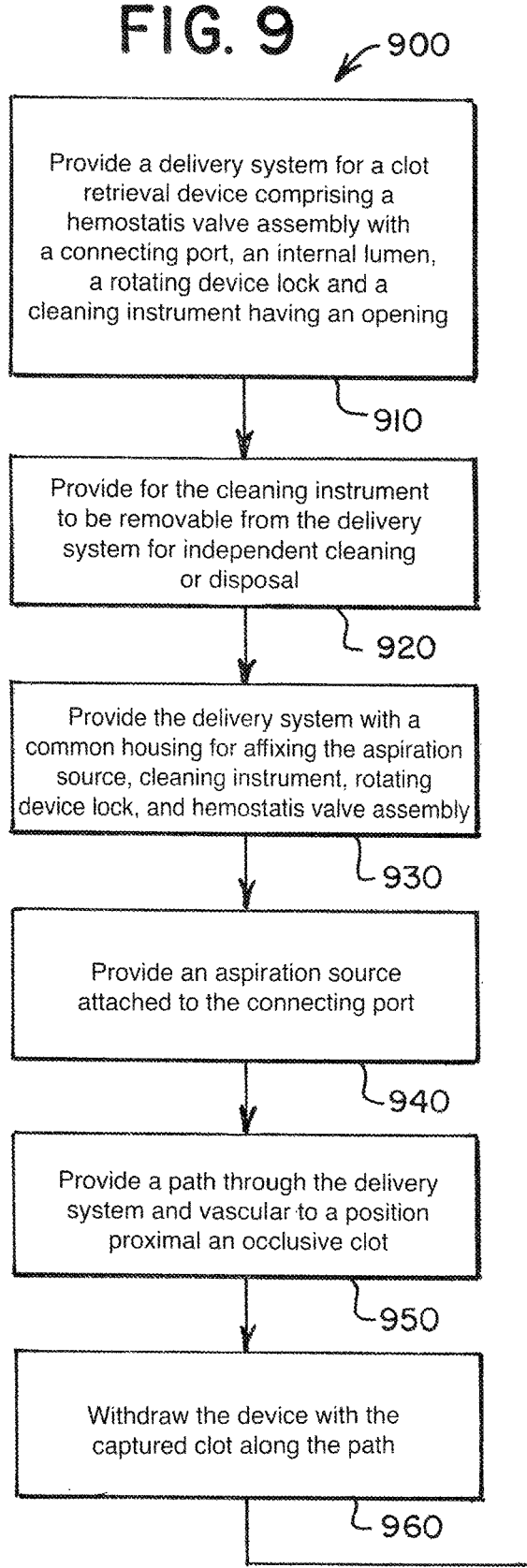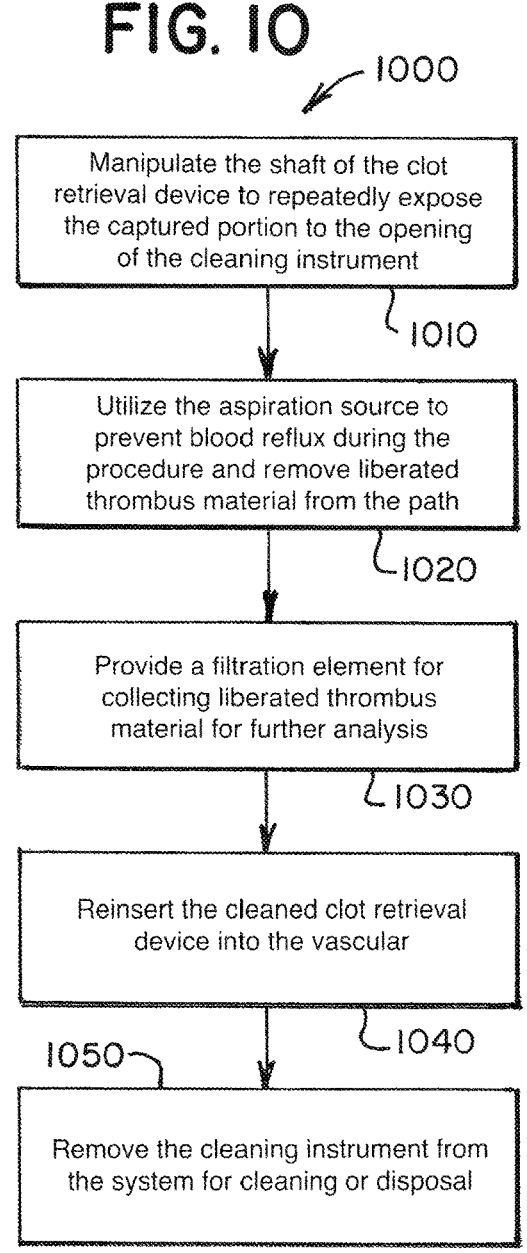

CLOT RETRIEVER CLEANING FOR REINSERTION

CROSS REFERENCE TO RELATED APPLICATION

The present application is a divisional application of U.S. patent application Ser. No. 16/508,452 filed Jul. 11, 2019. The entire contents of which are hereby incorporated by reference.

FIELD OF THE INVENTION

The present invention generally relates devices and methods for facilitating the cleaning of clot retrieval devices and other devices which remove acute blockages from blood vessels during intravascular medical treatments.

BACKGROUND

Clot retrieval devices are used in mechanical thrombectomy for endovascular intervention, particularly in cases where patients are suffering from conditions such as acute ischemic stroke (AIS), myocardial infarction (MI), and pulmonary embolism (PE). Multiple attempts at clot removal are often necessary, particularly in cases where relatively large clots form in particularly confined spaces of the vasculature, such as the cerebral passages.

Given the challenges in treating occlusive clots, significant attention has been given to the implements and practice. The mechanics of typical mechanical thrombectomy procedures involve slowing or reversing blood flow at a treatment site within a patient to aid in dislodgement and retrieval of a blood clot or thrombus material. A delivery system can have a source for direct aspiration into an intermediate or access catheter, which is often used in conjunction with a rotating hemostasis valve assembly and a clot retrieval device. This setup, while convenient for executing the procedure, also means the clot retrieval device typically must be fully removed from the delivery system for cleaning after each capture attempt. Cleaning is often performed manually by the physician, using a rag and/or a jet of saline from a syringe.

Further treatment challenges are presented by the body itself. In addition to tortuosity of the path associated with gaining access to a clot, the vasculature in the vicinity can often be fragile. Structural and functional diversity between the different vessels in the vascular tree result in variations in their associated biomechanical properties. For example, neurovascular vessels are often more delicate than similarly sized vessels in other parts of the body. The small size and fragile nature of these vessels can often be an impediment to clot retrieval devices. For example, stent-like clot retrievers (stentrievers) rely on applying a tensile radial force on the walls as a means of securely gripping an occlusion in preparation for removal. However, excessive force on the vessel walls can result in hemorrhage and perforations. Additionally, while a strong grip on the clot can be desirable during the critical initial steps of retrieval, when the clot is loosened from its lodgment, it can also make post-removal cleaning of the device more difficult and time-intensive.

The clot can be complex morphologies and consistencies, ranging from simple tube-shaped structures taking the shape of the vessel to long, strand-like arrangements that can span multiple vessels at one time. The age of a clot can also affect its compliance, with older clots tending to be less compressible than a fresh clot, and with the interaction of blood pressure more capable of distorting the vessel itself. Experience has also demonstrated that depending on the nature of the interaction with a clot retrieval device, the mechanical properties of a clot can be affected in a significant way.

Since thrombectomy procedures are highly time-sensitive, with increasing durations presenting escalating risks to patient, there is always a need for improved methods, devices, and systems for improving the speed and efficacy of these procedures. For many reasons, including some or all of the above, it is often necessary for physicians to adjust the procedure to meet challenges which are encountered. One impediment which prolongs the operation is that current devices and methods for the retrieval of clots often require a physician to make multiple attempts at material removal if an obstruction is not completely cleared on the initial attempt. Since the objective of the procedure is to remove the occlusive material and recanalize the vessel, the retrieval device must be cleared of captured debris before subsequent attempts can be made.

Presently there is no easy means of cleaning a retriever in situ between capture attempts, meaning the device must be completely removed from the body and delivery system for cleaning after each effort. Each time this is done, access to the target site is lost. Furthermore, this process adds time to the procedure because it necessitates the manipulation of the delivery system's valve gasket and potentially other accessory devices used in the operation, while also increasing the exposure to contamination. Existing devices and methods do not adequately or comprehensively address these challenges. The invention resolves them by placing a cleaning instrument in the removal path of the retrieval device. As a result, substantial time is saved in the cleaning of the devices, thereby increasing the chances of treatment success.

SUMMARY

It is an object of the present invention to provide systems, devices, and methods to meet the above-stated needs. Generally, it is an object of the present invention to provide a delivery system for a clot retrieval device and a cleaning instrument integrated into or mated with the delivery system positioned in the retrieval path of the clot retrieval device. The cleaning instrument has an opening or entrance passageway sized to receive the device in its deployed configuration and is intended to improve the process of preparing the device for reinsertion in to the vascular, thus facilitating further material capture attempts and shortening the overall duration of the invasive procedure.

The delivery system for the clot retrieval device could comprise a combination of one or more hemostasis valve assemblies, one or more wire gripping devices, and one or more controllable aspiration sources in series with an aspiration flow path. Rotating hemostasis valve assemblies facilitate the introduction of microcatheters, guidewires, and accessory devices, often through an intermediate or guide catheter, while minimizing back bleed and blood loss. This is accomplished by utilizing an entrance passageway into an internal lumen where catheters and other accessory devices are fed and then using a rotating adjustable gasket to maintain a hemostatically sealed condition. When open, the gasket allows devices to be introduced into the passageway. When closed and tightened, this gasket can control blood loss while also functioning as a device lock, applying a compressive grip on the device or devices to maintain a static position inside a blood vessel or the intermediate or guide catheter. Aspiration sources are typically connected to the side arm or connecting port of the rotating hemostasis valve assembly to provide and/or regulate a vacuum to one or more catheters. A syringe or vacuum pump can be connected to interface with the distal tip of the catheter through the catheter lumen and apply vacuum/aspiration as the clot is being retrieved. The connecting port can also be used for the introduction of a saline flush, injections of radiopaque contrast media, or other products and agents.

The methods and designs of devices in common usage for the capture and retrieval of clots are disclosed in prior art. Methods are disclosed for removing occlusive clots through the steps of providing a clot retrieval device having a clot engaging section with a constrained delivery configuration and an expanded deployed configuration. A microcatheter is advanced from a guide or intermediate catheter towards and across an occlusive clot. The device is loaded into the microcatheter and advanced to the occlusion, where it is deployed to capture the clot. The device and captured clot can then be retrieved in to a retrieval catheter and withdrawn from the vessel.

Various designs have been proposed for physically capturing the clot, and most clot retrieval devices share many common features and geometry. For example, US 2014/0371779, which claims priority to US Provisional 61/785,213 filed on Mar. 14, 2013, discloses an elongated member with an expandable clot engagement element which expands to extend across a clot to be captured. The design has stored potential energy in a folded, delivery configuration and expands to a deployed helical configuration when it exits a delivery microcatheter at the target site adjacent an occlusive clot. The engagement element can have inner and outer expandable members which can create a flow lumen across an occlusion when deployed, while also having a plurality of struts which imbed to provide a strong grip on the clot for the initial step of disengaging the clot from the vessel. To then retrieve the clot, it could be necessary to retract the device and clot proximally into a guide or intermediate catheter with a larger diameter. The device and clot can then either be withdrawn from the patient through the larger catheter or can be drawn back far enough to lodge a firmer clot in the tip or the larger catheter to be withdrawn in tandem. The control member a physician uses for manipulating such devices is often a wire, flexible shaft, or some other inner elongated member.

Other designs, such as a corkscrew-shaped device and constant aspiration models, are also common. One disclosed example involves having a guide catheter and an intermediate catheter with a distal mouth and configured such that it is advanceable within the lumen of the guide catheter. The intermediate catheter is advanced within a vessel to a position adjacent to an occlusive clot, at which point aspiration is applied to the proximal end of the guide catheter. The aspiration is directed through the distal lumen of the intermediate catheter to aspirate the clot into the mouth. The catheters and clot can then be retrieved together from the vasculature.

Regardless of the device used for capture, it is an object of the present invention to provide systems for then cleansing the device during withdrawal from the target site. In one example of the invention, the cleaning instrument is located with a rotating hemostasis valve assembly along the retrieval path and ready to receive the clot retrieval device while it is being withdrawn. The instrument has an opening or entrance passageway sized to receive the device in its deployed configuration. The retrieval path follows that of the delivery microcatheter substantially along the longitudinal centerline of the internal lumen of the hemostasis valve assembly. The retrieval process is accompanied by aspiration from a source connected to a connecting port of the hemostasis valve assembly. The cleaning instrument can be a variety of axial lengths and might or might not make physical contact with the retrieval device. The cleaning instrument can include brushes, fluid sprays, or other mechanisms that are positioned and configured to simultaneously clean around the circumference of the retrieval device as it is drawn along the retrieval path. Manipulation of the device along the removal path through the cleaning instrument is performed by applying a thrust force on the microcatheter and/or the device shaft.

Brush bristles can extend radially from the sidewall of the cleaning instrument, the bristles forming an opening or entrance that is substantially axisymmetric with the longitudinal axis of the rotating hemostasis valve assembly. The opening or entrance can be radially more restrictive than the internal lumen of the hemostasis valve assembly and can extend from the proximal end of the cleaning instrument to the distal end. The bristles can be of various lengths and shapes, and their formed opening can be of a cylindrical, tapered, or other geometry specific to the retrieval device used. In some examples the bristles can be of a simple, homogenous tubular structure. In other examples, depending on the composition of the clot or the shape of the retrieval device being used, it could be advantageous to tailor the flexure properties of the bristles through changes in shape and/or material composition. The bristles can therefore have a composite stiffness which varies three dimensionally along either the axial length of the cleaning instrument, radial length of the bristles from the longitudinal axis, or even radial position around the circumference of the opening.

The cleaning instrument can also be rotatable about the longitudinal axis of the internal lumen of the hemostasis valve assembly. A cleaning instrument disposed within a rotatable hub or collar can facilitate the removal of thrombus material from all angular points around the circumferential area of the device. Cleaning around the circumference could also aid in breaking up large pieces of clot material by varying the direction of the cleaning forces applied by the bristles. Smaller pieces of thrombus material are often more easily removed from the retrieval path through aspiration or filtration to help ensure they are not reintroduced into the vascular. In addition, a rotatable instrument can allow for changes in the density of the bristles, spray sources, or other cleaning elements. Similar to the previous example, device is moved along the removal path through the cleaning instrument by applying a thrust force on the device shaft extending from the distal end of the delivery system in the same way the retrieval device is delivered and removed from the vasculature. The device can be moved upstream and downstream through the cleaning instrument by alternating the direction of the applied force.

A further example apparatus can comprise a delivery system with a rotating hemostasis valve assembly and one or more body cavities separated by branch members disposed between them, allowing the body cavities to share the retrieval path. The branch members can incorporate seals capable of isolating individual body cavities from upstream or downstream fluids and/or pressure differentials. Each body cavity can also have one or more connecting port sharing a flow path with that body cavity, where the connecting ports are sized to receive a fluid injection or an aspiration source. In one example, when the clot retrieval device is withdrawn into a body cavity, heparinized saline or some other fluid can be injected through a first connecting port of the body cavity and used in conjunction with an aspiration source coupled to a second connecting port. Such a configuration can allow for the flushing and cleaning of a device in one or more body cavities independent of the others. Additional cleaning instruments, such as brushes or combs, can also be incorporated into the body cavities or elsewhere along the retrieval path.

Cleaning systems utilizing fluid spays or flushes can also be employed, many of which can have the advantage of not involving physical contact of solid objects with the device. Fluid sprays can be in gaseous or liquid form, or both, and modulated through regulators or throttling to both remove clot material from and sanitize the clot retrieval device prior to subsequent reinsertion into the vascular. The sprays could be delivered, for example, from a system of nozzles. The nozzles could be configured to spray simultaneously, or one or more nozzles could be operable independently of the other nozzles. For example, a system can include a plurality of nozzles disposed on a circumference in an annular pattern around the retrieval axis. The nozzles could be configured inside a housing or enclosure, which could have luer fittings allowing it to be mounted proximal to a hemostasis valve assembly. The enclosure could have a distal mouth situated along the retrieval path, sharing an axis with the longitudinal axis of the hemostasis valve assembly. As the clot retrieval device is drawn through the mouth, the nozzles could spray a fluid on the capture portion. A further advantage of such a system is that cleaning is directed around the entire circumferential area of the retrieval device. Fluid and liberated material debris can either be extracted through a vacuum source, or the cleaning instrument can be supplied with a filter or reservoir should it be desirable to collect the removed material for further laboratory analysis.

In many situations, it can be desirable for the cleaning instrument to be easily removable from the delivery system such that it can more rapidly be cleaned and/or replaced independent of the system. In one example of the invention, the cleaning device can be connected in series with the hemostasis valve assembly using a luer or threaded connection. In other examples of the invention, the removed cleaning instrument can be disposable, eliminating the need to sanitize it between procedures. In still other examples, material liberated from the clot retrieval device can become lodged with the cleaning instrument. Removal of the instrument can allow this material to be collected for further histological laboratory analysis or disposal. Removability also allows the physician the option of selecting and using cleaning devices of multiple configurations during the same procedure, thereby improving the chances of treatment success.

An example method for cleaning a clot retrieval device in preparation for reinsertion into a patient can include some or all of the following steps and variations thereof. The steps are recited in no particular order. A delivery system for a clot retrieval device can have a hemostasis valve assembly with a connecting port, an internal lumen, a rotating device lock, and a cleaning instrument with an opening sized to receive the clot retrieval device can be provided. An aspiration source, often comprising a vacuum pump or syringe, can be provided and connected to the connecting port of the hemostasis valve assembly. A path through the delivery system and vascular to a position proximal an occlusive clot can be provided, and the cleaning instrument can be positioned in the path. The clot retrieval device with a captured clot can be withdrawn along the path.

The cleaning instrument can be utilized to liberate the clot material from the capture portion of the clot retrieval device while the device remains along the path internal to the delivery system. The cleaning instrument can be disposed to clean the entire circumferential area of the capture portion. During the cleaning process, the physician can manipulate the device to allow for repeated exposure of the device to the cleaning instrument, helping ensure the efficacy of the cleaning process. The aspiration source can be utilized to prevent blood reflux and to remove liberated thrombus material from the path. When desirable, the liberated thrombus material can be filtered and collected for further laboratory analysis.

When cleaning is complete, the clot retrieval device can be reinserted into the vascular for additional capture attempts. The cleaning instrument can further be removed from the system for independent cleaning or disposal, either between capture attempts or at the conclusion of the procedure.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with the following description of the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combining elements from multiple figures to better suit the needs of the user.

FIG. 1 is an illustration of a system for cleaning a clot retrieval device with a delivery system with a cleaning instrument configured within a rotating hemostasis valve assembly according to aspects of the present invention;

FIGS. 2a-2b shows multiple views of a removable cleaning instrument with bristles, and how the instrument is integrated into and shares a clot retrieval path with a hemostasis valve assembly according to aspects of the present invention;

FIGS. 3a-3c shows an example of the interaction between a cleaning instrument and a clot retrieval device with a captured clot as the device is drawn along the retrieval path;

FIGS. 4a-4b are side and cross section views of a cleaning instrument disposed along the retrieval path within a rotatable hub according to aspects of the present invention;

FIGS. 5a-5b is an illustration of a system including a cleaning instrument and a hemostasis valve assembly has multiple body cavities and configured to receive fluid injection and aspiration sources;

FIGS. 9-10 are flow diagrams each outlining a method for cleaning a clot retrieval device in preparation for reinsertion into the vascular according to aspects of the present invention.

DETAILED DESCRIPTION

Figure 4B:
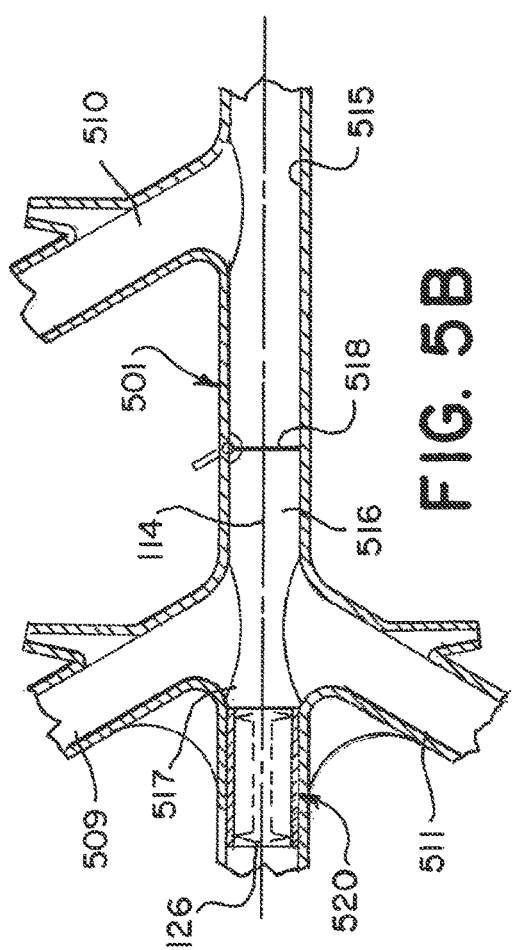

Specific examples of the present invention are now described in detail with reference to the Figures, where identical reference numbers indicate elements which are functionally similar or identical. However, the invention is not limited to the examples described, which can be varied in construction and detail. The terms "distal" and "proximal" are used throughout the following description and are meant to refer to a positions and directions relative to a treating physician. As such, "distal" or "distally" refer to a position distant to or a direction away from the physician. Similarly, "proximal" or "proximally" refer to a position near to or a direction towards the physician.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

Accessing the various vessels within the vascular, whether they are coronary, pulmonary, or cerebral, involves well-known procedural steps and the use of a number of conventional, commercially-available products. These access products, such as catheters, microcatheters, angiographic materials, and guidewires are widely used in laboratory and medical procedures. When these products are employed in conjunction with the system and methods of this invention in the description below, their function and exact constitution are not described in detail.

The clot retrieval device mentioned throughout this description can be any of a number of commercially available products, and most of those share many common features. Devices which compress the clot upon capture tend to make it firmer, or "stickier", which can complicate retrieval. Other devices are meant to expand between the clot and the vessel in such a way as to minimize compression while loosening the clot from the vessel wall. No matter how the clot properties evolve after capture, they influence the level of grip the retrieval device can exert and subsequently how they are then liberated from the device during the cleaning process. It is an advantage of this design to allow interaction with the complete circumferential area of the device while offering a high degree of flexibility to the treating physician. The design's ability to allow more rapid follow-up retrieval attempts lessens the potential negative effects of clot properties and other details which can be beyond the physician's power to control.

FIG. 1 illustrates a clot retrieval system 100 of this invention with a cleaning instrument 120 being used in the retrieval of a clot 40 from the blood vessel 20 of a patient. A guide catheter can be used to direct devices to the target site. The clot retrieval device 60 can deploy from the distal end 72 of a delivery microcatheter 70 and can include an elongate proximal shaft 64 with an expanding distal receptor portion 62 for capturing the clot. The delivery system comprises a rotating hemostasis valve assembly 101 having a distal end 102 with an opening sized for and hemostatically sealing the delivery catheter 70, a proximal end 104, and an internal lumen 108. The cleaning instrument 120, with an entrance or passageway sized to receive the clot retrieval device 60, can be disposed along and share a retrieval path of the clot retriever device with the hemostasis valve assembly 101. The assembly can have one or more of a connecting port 110, which can be sized and used for connecting an aspiration source, but which can also be configured for other functions, such as fluid injection. Typically, a control valve is included to regulate the flow of aspirated blood or other fluid.

Deployment of the clot retrieval device 60, as well as the location of the device during retraction and in preparation for and during cleaning, can be aided by the application of a radiopaque compound, or the placement of radiopaque markers 68 on the delivery microcatheter 70, guide catheter, and/or the clot retrieval device. For example, a radiopaque compound could be incorporated on the receptor portion 62, or one or more radiopaque markers 68 could be added near the distal end of the elongate shaft 66 both distal and proximal to the receptor portion to mark for the physician the terminal ends of the device during the procedure. Suitable practices are frequently used in connection with other devices and implants and are well known in the art.

The rotating hemostasis valve assembly 101 defines a longitudinal axis 114 extending along the internal lumen 108 from the proximal end 104 to the distal end 102 of the valve assembly. The rotating device lock 112 of the hemostasis valve assembly 101 can be articulated through closed, semi-open, and/or open conditions of the gasket or seal. When the rotating device lock 112 is in the semi-open position, accessories passing through the hemostasis valve assembly 101, such as a shaft 64 of the clot retrieval device 60, can be retracted or conveyed through a lumen of a delivery microcatheter 70. Care must be taken with the positioning of the gasket. The efficacy of applied aspiration will decline if there is air leakage through the gasket around the shaft 64. However, if the gasket is too tight around the shaft it can inhibit the shaft from being freely and/or properly articulated during a treatment. When in the semi-open condition, the gasket of the rotating device lock 112 provides sufficient sealing to prevent air ingress when a vacuum is applied to a connecting port 110 of the hemostasis valve assembly during aspiration. In one example thrombectomy procedure, a clot retrieval device 60 can capture a clot 40 and be retracted into a guide catheter while the catheter is under vacuum without air leakage through the gasket of the rotating device lock 112.

FIG. 2a illustrates the cleaning instrument 120 of the clot retrieval system 100 of this invention. The cleaning instrument 120 can have bristle elements 124 which extend radially inwards from the sidewall 122 of the instrument and form an opening 126 that is coaxial with the longitudinal axis of the hemostasis valve assembly. The opening extends from the proximal end of the cleaning instrument to the distal end of the cleaning instrument. An advantage of a bristle configuration is that a clot retrieval device can have less axial stiffness at the distal end, which offers deliverability advantages, since the device can self-center in the instrument during subsequent cleaning.

As seen in the cross-sectional view in FIG. 2b, the opening 126 defined by the bristles 124 can be radially more restrictive than the internal lumen 108 of the hemostasis valve assembly 101. The bristles can have a volumetric opening along the length of the instrument that is a simplistic homogenous cylindrical structure as in this construction, or could be a more complex tapered, conical, or other geometry better suited to the shape of the retrieval device used. In a preferred example, the stiffness and flexure properties of the bristles are tailored to the expected stability of the clot to be captured, for example when the clot is especially firm with a high fibrin content. In this way the cleaning instrument can be adaptable to the needs of the respective treatment to allow for enhanced efficiency.

The cleaning instrument shown in the figures is used to illustrate one aspect of the present invention. Of course, the present invention can be applied to a cleaning instrument of any shape or size and could be made from several sections.

Collectively FIG. 3a-FIG. 3c shows side views of an example sequence where a clot retrieval device 60 is drawn through a cleaning instrument 120 with bristles 124. The instrument can be disposed within the internal lumen 108 of a hemostasis valve assembly. The bristles can be radially more restrictive than the internal lumen and sized for the capture or receptor portion 62 of the clot retrieval device 60. The physician uses the shaft 64 of the device to withdraw the device from downstream along the retrieval path. FIG. 3b shows the device as it approaches the cleaning instrument, moving through the lumen towards the proximal end of the hemostasis valve assembly. The capture or receptor portion 62 shown in this figure comprises a plurality of struts and can have a captured clot 40 but might also contain smaller thrombus material 42 or debris from the vasculature located at various radial positions around its circumference. The physician can manipulate the device through the bristles proximally and distally as many times as necessary until the receptor portion 62 is clear and the debris 42 has been liberated.

It can be necessary to use a vacuum source to reverse flow in the vasculature during this retrieval process to prevent the escape and distal passage of and clot fragments liberated during cleaning. This negative pressure differential can be maintained, or even increased, after the material is liberated from the device to further remove the material from the retrieval path and lumen. The vacuum can then be further changed or removed when the clot retrieval device is reintroduced into the vasculature to complete the recanalization of the patient's vessel.

FIG. 4a depicts a side view of another example of a system 400. Like previous examples, a clot retrieval device is withdrawn along the retrieval path through an internal lumen 108 from the distal end 102 toward the proximal end 104 of a hemostasis valve assembly 101. A cleaning instrument 120 is disposed within a rotatable hub 460. The hub can have one or more fittings 462 and 464, such as luer connectors, at the distal and proximal ends of the hub for ease of interface with the system, allowing it to rotate about the longitudinal axis 114 of the hemostasis valve assembly 101. The fittings also allow the hub to be easily detachable from the hemostasis valve assembly. Such a system offers many advantages. It allows the hub to be mated with any standard hemostasis valve assembly which is configured with connection fittings at its proximal and/or distal ends. The physician can rotate the hub as much as necessary to remove especially obstinate clot material around the entire circumferential area of the device. Removal of the clot material from the system 400 can then be accomplished by using a vacuum source (not shown in this figure) connected to a connecting port 110 of the hemostasis valve assembly 101. In a favored example, the cleaning instrument is located proximal to the connecting port. Alternatively, the physician can allow the debris to remain within the hub, which can be rapidly removed from the hemostasis valve assembly through manipulation of the distal fitting 462. The hub can then be cleaned or disposed independently, and, if desirable, the clot material collected for further analysis.

FIG. 4b illustrates a cutaway view of the hub 460 showing the cleaning instrument 120 disposed within. The optimal dimensions of the cleaning instrument and bristles 124 depend very much on the dimensions of the clot retrieval device and the target clot itself. In one example, the bristles 124 are disposed around the complete circumference of the cleaning instrument sidewall 122. In another example, the bristles can be disposed only at selected clocking positions around the circumference of the instrument sidewall. The bristles again can have a volumetric opening along the length of the instrument that is a simplistic homogenous tubular structure or could be a more complex tapered, conical, or other geometry better suited to the shape of the retrieval device used. As described in previous examples of the invention, the stiffness and flexure properties of the bristles can be tailored to the stability and firmness of the clot to be captured, and even be configured to have a compound stiffness if desirable.

In this configuration, it is even possible for the physician to substitute cleaning instruments mid-procedure if initial cleaning proves unsuccessful or inefficient. A first cleaning instrument could be removed through manipulation of the distal fitting of the hub, and a second cleaning instrument with different characteristics or properties could then be attached to the hemostasis valve assembly.

It is an objective of the invention to eliminate the need for handling of the device or removing it from the delivery system between retrieval attempts, while also maintaining sterility and a high level of cleaning proficiency. Further aggregation and breakup of the clot during cleaning can facilitate its evacuation from the system. There are a number of commonly used methods to clear the cannulas of arterial and intravenous lines, both to sterilize and prevent clotting and blockage, which could be employed to aid in the removal and separation of a clot captured in the clot retrieval device. Flushes such as saline or heparinized saline are often employed. Breaking down the clot can be accomplished through the introduction of fibrinolysis contributors like tissue plasminogen activator (tPA), such as alteplase, reteplase, and tenecteplase.

Figure 5B:
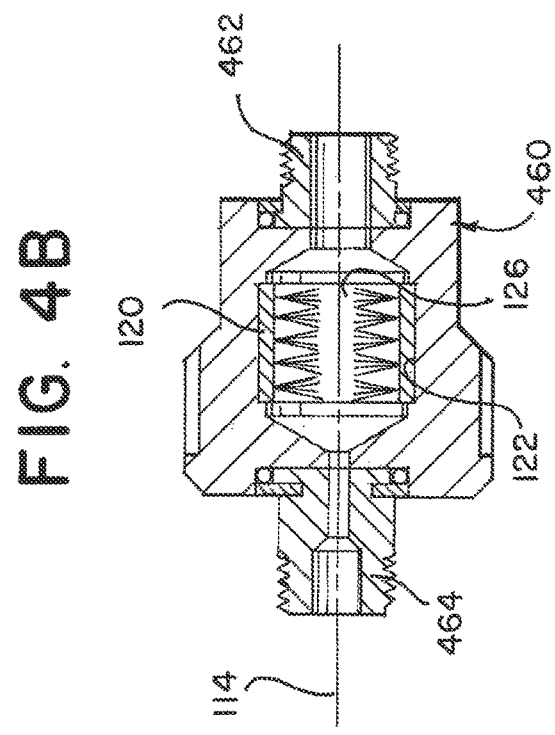

In another case shown in FIG. 5, the system 500 can include a rotating hemostasis valve assembly 501 comprising a proximal end 104, a distal end 102 sized for a delivery microcatheter, a rotating device lock 112, a longitudinal centerline 114, and at least two internal body cavities separated by one or more central branches 516. The central branch can have a closeable mechanical seal or gasket 518 disposed within. In one example, the hemostasis valve assembly can have a first body cavity 515 and a second body cavity 517 proximal to the first body cavity and sharing the retrieval path of the clot retrieval device. When the seal 518 is open, the first body cavity and the second body cavity share a common flow path. When the seal is closed, the common flow path is divided into a first flow path in the first body cavity isolated from a second flow path in the second body cavity. The first body cavity can have at least one connecting port 510 sharing a flow path with the first body cavity and sized to receive an aspiration source, such as a vacuum pump or syringe. The second body cavity can have at least a first connecting port 509 and a second connecting port 511, each of the first and second connecting points sharing a flow path with the second body cavity. The first connecting port 509 or the second body cavity can be sized to receive a fluid injection, such as water, heparinized saline, and/or tPA, and configured to flush the second body cavity when the clot retrieval device is withdrawn therein. The second connecting port 511 of the second body cavity is sized to receive an aspiration source for evacuating the contents of the second body cavity. The aspiration source can be the same as that connected to the connecting port 510 of the first body cavity, or it can be a second source, allowing the vacuum pressure drawn in the second body cavity to differ from that drawn in the first body cavity. The seal 518 prevents the contents of the second body cavity from migrating back downstream. If desired, further connecting ports can be configured into the flanks of the hemostasis valve assembly 501 to allow additional procedural flexibility to the physician.

A bristled cleaning instrument 520 could also be further integrated with the hemostasis valve assembly 501 in this example. Alternately, the cleaning instrument could be disposed within a rotatable hub as seen in the previous system 400 and connected to the system 500. The cleaning instrument could be used in concert with the fluid flush to aid in removing the clot material from the retrieval device.

Figure 6:
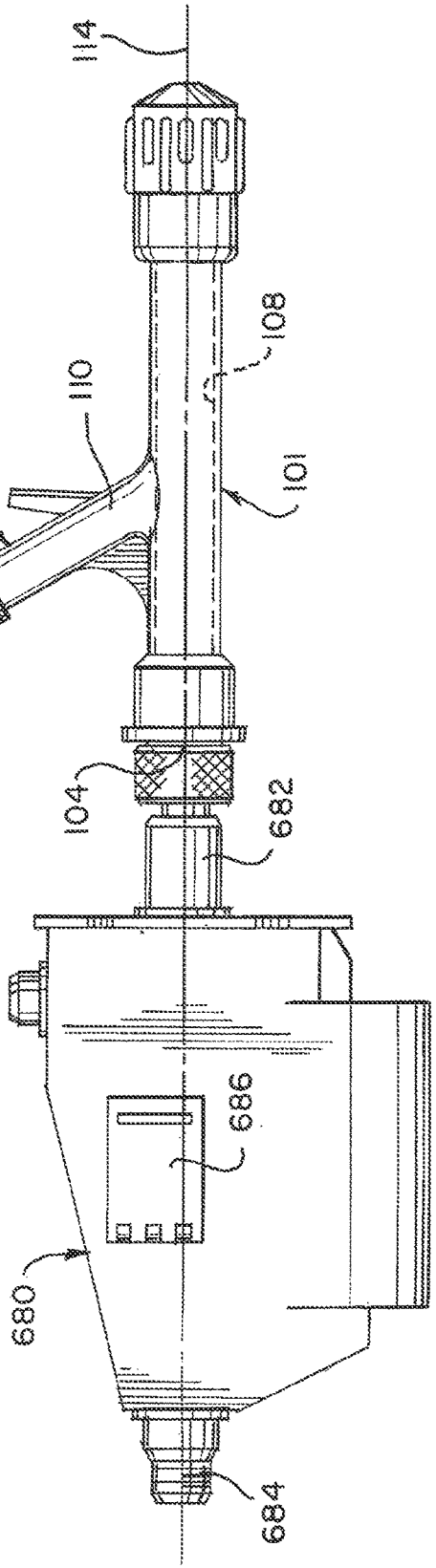
FIG. 6 shows a system where a removable enclosure has a cleaning instrument integrated with a hemostasis valve assembly to share the retrieval path.

In a further example, the system 600 shown in FIG. 6 comprises a housing or enclosure 680 integrated with a hemostasis valve assembly 101. The enclosure is configured to mount upstream of and proximal to a proximal end 104 of the hemostasis valve assembly. The enclosure can have distal and proximal fittings 682, 684, such as luer connections, for coupling and decoupling from the hemostasis valve assembly 101 or other devices in the delivery system. As in previous examples, the hemostasis valve assembly has a connecting port 110 for attaching an aspiration source. The hemostasis valve assembly can also have a distal end 102 sized for a delivery catheter and an internal lumen 108 with a longitudinal axis 114 along the retrieval path of a clot retrieval device.

Figure 7:
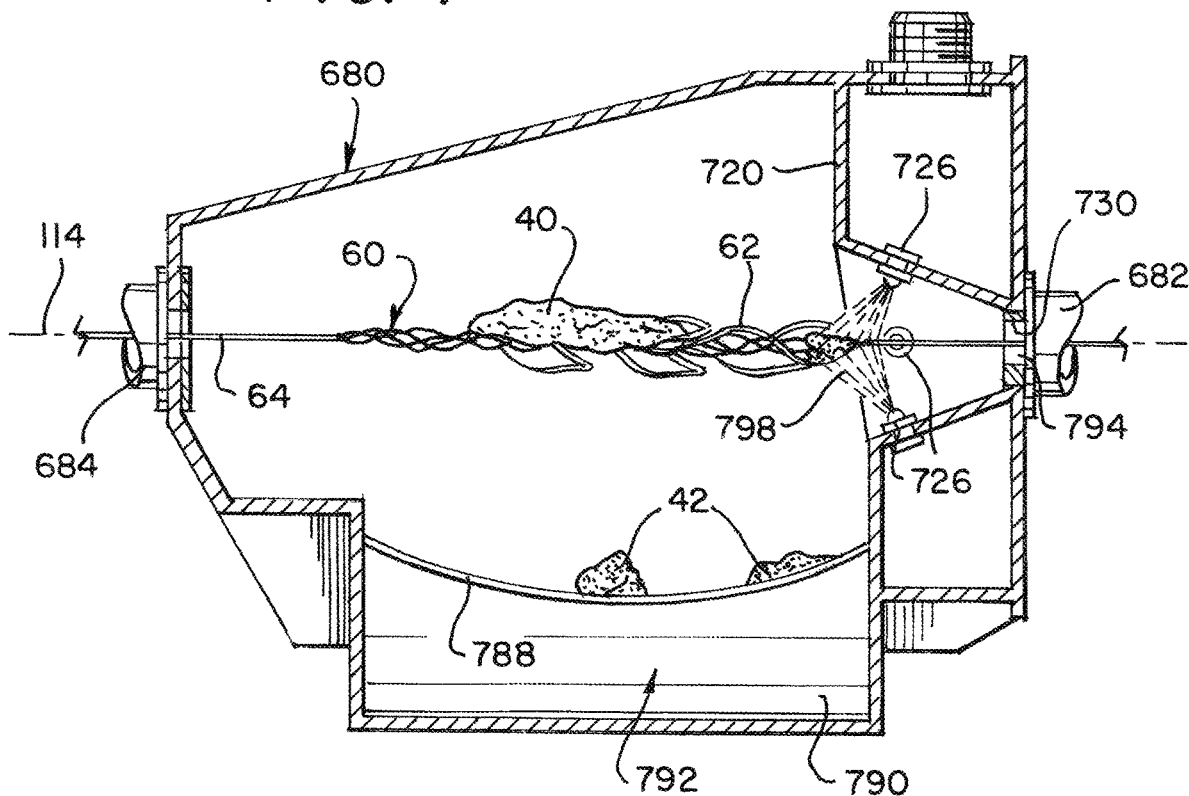
FIG. 7 is a side view of an enclosure from FIG. 6 having a cleaning instrument and collection apparatus according to aspects of the present invention.

A view internal to the enclosure 680 of system 600 is shown in FIG. 7. The enclosure can have a distal mouth 794 with a circumferential opening 730 sharing an axis with the longitudinal axis 114 of the hemostasis valve assembly and the retrieval path. Proximal to the mouth, a cleaning instrument 720 can include a plurality of nozzles 726 disposed in an annular pattern around the axis 114 and configured to spray 798 fluid on the circumferential area of the clot retrieval device 60 as it is withdrawn along the retrieval path. This allows the cleaning process to be conducted without physical contact, other than the fluid, and without exposing the device to contaminants outside of the system. As in previous examples, articulation of the clot retrieval device using the shaft 64 allows for both repeated exposure to the spray of the cleaning instrument, or for the device to dwell in the spray if a dissolutive fibrinolysis agent such as tPA is used in the system.

Figure 8A:
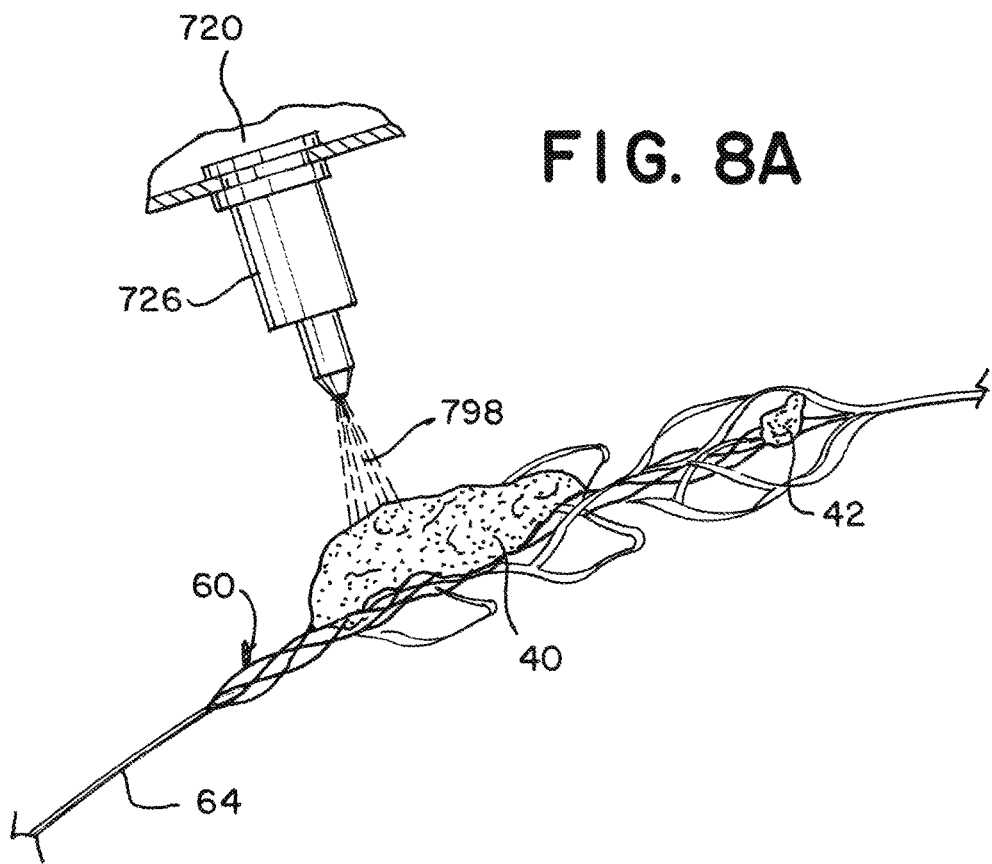
FIGS. 8a-8c are illustrations of spray nozzles cleaning a clot retrieval device with captured clot according to aspects of the present invention.

The nozzles 726 could be configured to spray 798 simultaneously in a balanced form, or one or more nozzles could be operable independently of the other nozzles. The incident angle of the spray on the capture portion 62 of the retrieval device can be varied from nozzle to nozzle, ranging from nearly perpendicular to the retrieval path, as shown in FIG. 8a, to a substantially more oblique angle. Such an arrangement further offers the advantage of exposing more surface area of the clot 40 to the spray 798 while altering the direction of forces acting on the clot from the spray. The spray can be gaseous or liquid form, or both, and modulated through throttling to vary the volumetric flow rate. The spray can be configured to both remove clot material from the capture portion 62 and sanitize the clot retrieval device prior to subsequent reinsertion into the vascular.

The enclosure shown FIG. 6 and FIG. 7 is used to illustrate an example according to aspects of the present invention. Of course, the present invention can be applied to an enclosure of any shape or size and could be made from several sections and made of materials allowing a user to see inside. The enclosure might or might not be symmetrical so long as it lies on the retrieval path.

Fluid and liberated material debris 42 can either be removed through the vacuum source, or the enclosure 680 can further include a collection apparatus 792 with a filter 788 and collection reservoir or basin 790 should it be desirable to collect the removed clot material for further laboratory analysis. The collection apparatus 792 could have threads or some other means of attaching to the enclosure, allowing it to be removed at any point during a mechanical thrombectomy procedure.

Laboratory analysis can include clot analysis such as some or all of a range of steps, without limitation: blood tests, non-contrast computerized tomography (CT) scan, including quantitative methods to analyze stroke severity, such as Alberta stroke program early CT score (e.g., ASPECTS), and automatic assessments of ASPECTS using software (e-ASPECTS), considering the patient's clinical history, stroke severity, such as the National Institute of Health Stroke Severity (NIHSS) clinical exam and/or neurological exam.

The clinical history of the patient can include factors such as whether the patient is aged between 18 years and 85 years; an mRS score of 0 or 1; angiographic confirmation of an occlusion of an internal carotid artery (ICA) (including T or L occlusions), M1 or M2 MCA, VA, or BA with mTICI flow of 0-1; MRI criterion: volume of diffusion restriction visually assessed ≤50 mL.; CT criterion that includes an ASPECTS score of 6 to 10 on baseline CT or CTA-source images, or, volume of significantly lowered. CBV≤50 mL; life expectancy likely less than 6 months; females who were pregnant or breastfeeding; history of severe allergy to contrast medium; known nickel allergy at time of treatment; known current use of cocaine at time of treatment; patient has suffered a stroke in the past 3 months; the patient presents with an NIHSS score <8 or >25 or is physician assessed as being in a clinically relevant uninterrupted coma; the use of warfarin anticoagulation or any Novel Anticoagulant with International Normalized Ratio (INR) >3.0; platelet count <50,000/μL; glucose <50 mg/dL; any known hemorrhagic or coagulation deficiency; unstable renal failure with serum creatinine >3.0 or Glomerular Filtration Rate (GFR) <30; patients who received a direct thrombin inhibitor within the last 48 hours; a partial thromboplastin time (PTT) less than 1.5 times the normal to be eligible; patients with severe hypertension on presentation (SBP >220 mmHg and/or DBP >120 mm Hg); cerebral vasculitis; improving neurological status; clinical symptoms suggestive of bilateral stroke or stroke in multiple territories; ongoing seizure due to stroke; evidence of active systemic infection; cancer with metastases; CT or MRI evidence of recent hemorrhage on presentation; baseline CT or MRI showing mass effect or intracranial tumor (except small meningioma); suspicion of aortic dissection, presumed septic embolus, or suspicion of bacterial endocarditis; stenosis, or any occlusion, in a proximal vessel that requires treatment or prevents access to the site of occlusion; evidence of dissection in the extra or intracranial cerebral arteries; and/or occlusions in multiple vascular territories (e.g., bilateral anterior circulation, or anterior/posterior circulation).

Laboratory analysis can also include CT scanning whereby one normal X-ray and also a second less powerful X-ray are used concurrently to make the images. The two X-rays will generate different spectra using different tube potentials. One approach that uses CT scanning as described in U.S. application Ser. No. 16/001,427, is incorporated by reference in its entirety as if set forth verbatim herein. The use of MRI and/or advanced MR images of the patient's brain to evaluate the clot are also contemplated in connection with the laboratory analysis here. Advanced MR images can include sophisticated magnetic resonance imaging techniques that evaluate freedom of water molecule movement in a selected area, the microvascular integrity and hemodynamic characteristics, and the chemical makeup of the clot. Advanced MR can include perfusion imaging, diffusion-weighted imaging, and MR spectroscopy, as well as magnetic resonance angiography, and/or magnetic resonance venography.

Laboratory analysis can also include carotid ultrasound, cerebral angiogram, echocardiogram, intravascular ultrasound (IVUS), and/or optical coherence tomography (OCT).

Laboratory analysis can also include one or more blood tests as well as a non-contrast and/or contrast CT scan of the patient, including the brain area to look at the structures of the brain and evaluate the clot or clots, particularly since no preparation is required for the patient.

As for analyzing liberated material debris 42 in the fluid reservoir 790 or lodged in the filter 788, analysis can also include spectroscopic techniques such as Near Infrared Spectroscopy (NIR) and/or Raman spectroscopy to produce a spectrum that relates to the chemical composition and physical properties of the respective occlusion. In this respect, information contained in the spectral bands can be interpreted to provide almost instant analysis of the nature of the material being tested. In certain embodiments, instrumentation associated with the NIR and/or Raman spectroscopy can be included in a microcatheter associated with the clot retrieval system.

Laboratory analysis can also include scanning fluid and liberated material debris 42 with a catheter having a fiberoptic bundle core connected to a NIR or Raman spectrophotometer. A spectrum of the transmitted light can be generated, and this information can be used to predict the composition of the material that the light was reflected from. For example, chemical information that corresponds to the bulk composition of the clot can be deciphered from light absorptions in the near infrared portion of the electromagnetic spectrum and can be used to measure the relative composition of RBC, water, fibrin, or the like within the clot. Physical information that can be detected in this embodiment can relate to the compactness and organization in the clot resulting from scattering and diffusion of light.

Figure 8B:
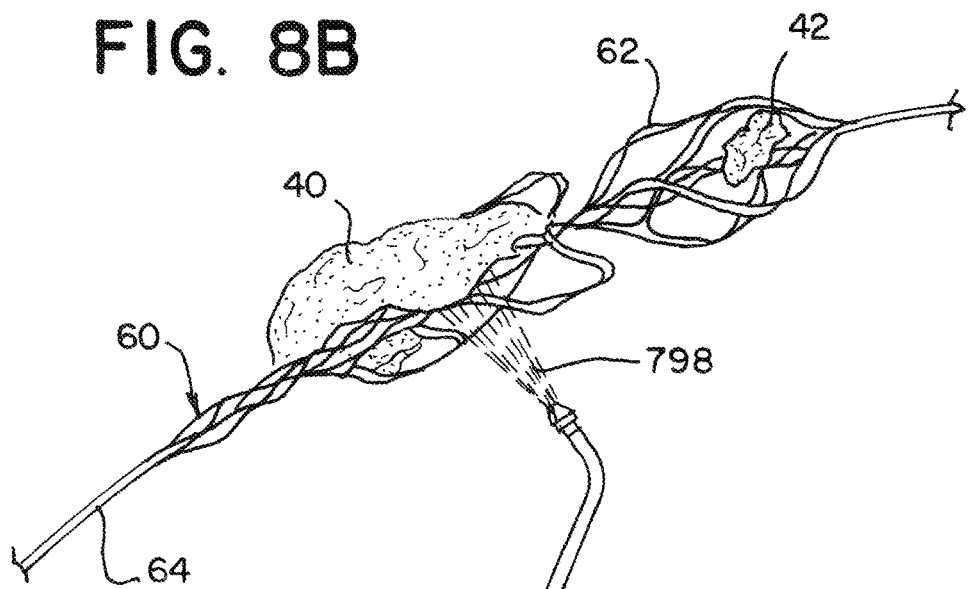
Figure 8C:
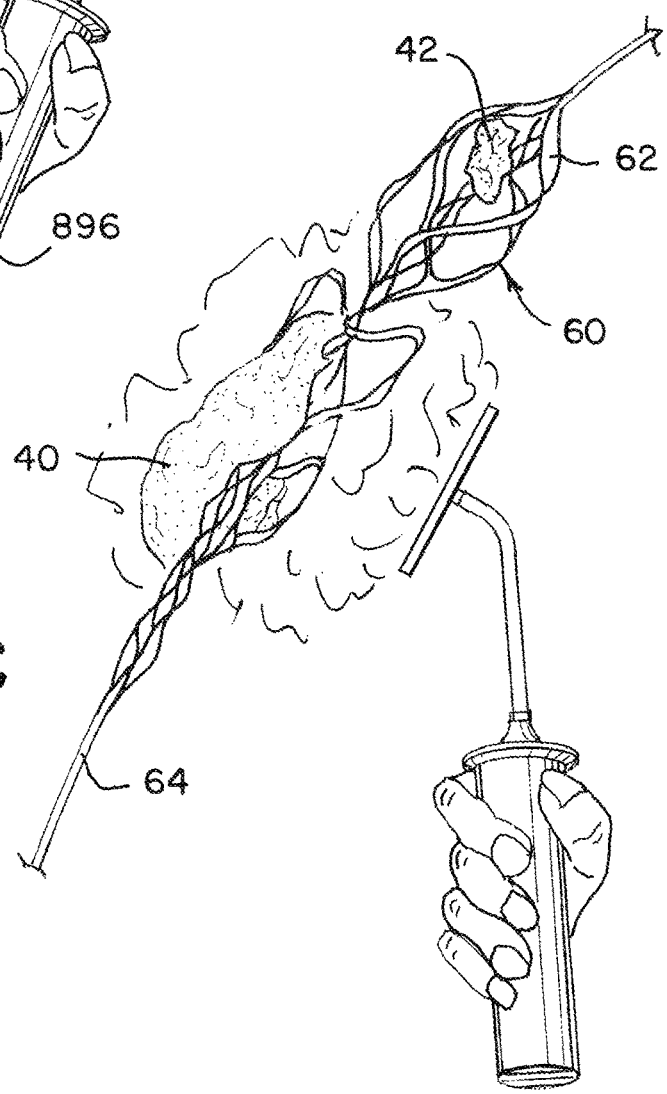

Laboratory analysis can also include determining criteria associated with fluid and liberated material debris 42. For example, a red blood cell count, a white blood cell count, serum level, fibrin level, or the like can be established to classify the clot. A sample of the clot can then undergo visual or tactile analysis to assist in selection of the proper device used for further procedures. An indication of clot composition can be provided that advantageously allows classification of the clot in both qualitative and quantitative terms as follows, including the exclusion of presence of a hemorrhagic stroke. Such information can include cellular constituents, extracellular constituents, morphology, organization and distribution of components, permeability, adhesion, water content, resistance to degradation, fibrin crosslink density, fiber diameter, modulus, strain, deformation (e.g., elastic, plastic, viscoelastic), compressibility, and/or fracture behavior. An example table of such indications is provided herein without limitation and other qualitative and/or quantitative indications are contemplated for use with the herein disclosed embodiments:

The enclosure 680 of system 600 can further comprise an access port 686 for admittance into the interior of the enclosure without removing it from the hemostasis valve assembly. The access port can be any of a variety of shapes and can have a cover that could be hinged or slidable to seal the port when not in use. The access port can allow a physician to perform targeted functions without removing the clot retrieval device from the system 600. For example, obstinate clots can be targeted with methods to further encourage fibrinolysis. As additionally shown in FIG. 8b, manually articulated spray nozzles 896 can be introduced to augment the spray 798 pattern of the cleaning instrument 720. For example, thrombus fragments 42 lodged in a more isolated segment of the capture portion 62 of the clot retrieval device 60 to be selectively targeted. FIG. 8c further shows the access port can further allow for the selective application of heat, or alternate means of sterilization such as steam, ultraviolet radiation, or gas vapor sterilants (e.g. ethylene oxide, ozone).

The system 600 can be designed according to examples and principles disclosed herein and need not be specifically designed or shaped as illustrated in the enclosed figures.

FIG. 9 and FIG. 10 are flow diagrams each comprising method steps for cleaning a clot retrieval device in preparation for reinsertion into the vascular of a patient for successive capture attempts. The method steps can be implemented by any of the example systems, devices, and/or apparatus described herein or by a means that would be known to one of ordinary skill in the art.

Referring to a method 900 outlined in FIG. 9, step 910 describes providing a delivery system for a clot retrieval device which comprises a hemostasis valve assembly with one or more connecting ports, an internal lumen, a rotating device lock, and a cleaning instrument having an opening sized to receive the clot retrieval device. In step 920, the cleaning instrument is removable from the delivery system. In step 930, the delivery system has a common housing for integrating an aspiration source, the cleaning instrument, the rotating device lock, and the hemostasis valve assembly. In step 940, the aspiration source, commonly a vacuum pump or syringe, is affixed to the connecting port of the hemostasis valve assembly.

In step 950, a path through the delivery system and the patient's vascular to a position proximal to an occlusive clot is defined. A clot retrieval device is used to capture a clot and is retrieved using conventionally known techniques. In step 960, the clot retrieval device is withdrawn with the captured clot along the path. While the device is along the path and internal to the delivery system, in step 970 the cleaning instrument is utilized to liberate the captured clot material from the capture portion of the clot retrieval device.

Referring the method 1000 outlined in FIG. 10, in step 1010 the physician manipulates the shaft or control member of the clot retrieval device to repeatedly expose the capture portion of the device to the cleaning instrument. In step 1020, the aspiration source is used to prevent blood reflux while also removing liberated thrombus material from the retrieval path. In step 1030, a filtration element is provided within the system to collect clot material and debris for further laboratory analysis. In step 1040, the cleaned clot retrieval device is reinserted into the vascular for a subsequent capture attempt on additional thrombus material. The cleaning instrument is removed from the system for cleaning and or disposal in step 1050.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It must also be noted that, as used in the specification and the appended claims, the singular forms "a," "an," and "the" include plural referents unless the context clearly dictates otherwise. Ranges can be expressed herein as from "about" or "approximately" one particular value and/or to "about" or "approximately" another particular value. When such a range is expressed, other exemplary embodiments include from the one particular value and/or to the other particular value.

Some references, which can include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The descriptions contained herein are examples of embodiments of the invention and are not intended in any way to limit the scope of the invention. While particular examples of the present invention are described, various modifications to devices and methods can be made without departing from the scope and spirit of the invention. For example, while the examples described herein refer to particular components, the invention includes other examples utilizing various combinations of components to achieve a described functionality, utilizing alternative materials to achieve a described functionality, combining components from the various examples, combining components from the various example with known components, etc. The invention contemplates substitutions of component parts illustrated herein with other well-known and commercially-available products. To those having ordinary skill in the art to which this invention relates, these modifications are often apparent and are intended to be within the scope of the claims which follow.

The invention claimed is:

1. A system for cleaning a blood clot retrieval device along a retrieval path without physical contact, the system comprising:
    the blood clot retrieval device;
    a delivery catheter;
    a hemostasis valve assembly;
    an enclosure comprising a distal mouth sized for receiving the blood clot retrieval device and captured blood clot, the mouth having an axis located along the retrieval path;
    a circumference around the axis; and
    a cleaning instrument residing circumferentially around the mouth of the enclosure, the cleaning instrument sharing but not obstructing the retrieval path, wherein the cleaning instrument comprises a plurality of nozzles, each nozzle circumferentially distributed in an annulus around the circumference and sized to spray a fluid on the circumferential area of a capture portion of the blood clot retrieval device as it is drawn through the mouth along the retrieval path, and wherein one or more nozzles are configured to be operable independently of the other nozzles.

2. The system of claim 1, wherein the enclosure further comprises fittings for mating the enclosure with the hemostasis valve assembly, and wherein the mouth axis is aligned with a longitudinal axis of the hemostasis valve assembly.

3. The system of claim 1, wherein the enclosure further comprises a collection apparatus, the collection apparatus comprising:
    a filtration element to capture liberated thrombus material; and
    a collection basin to collect fluid which passes through the filtration element.

4. The system of claim 3, wherein the collection apparatus is removably attached to the enclosure.

5. The system of claim 1, wherein the enclosure further comprises an access port, the port configured for:
    manual articulation of an external spray nozzle; and
    the introduction of sterilization media for sterilizing the blood clot retrieval device.

6. The system of claim 5, wherein the access port comprises a cover that is hinged or slidable to seal the port when not in use.

7. The system of claim 1, wherein the hemostasis valve assembly comprises:
    a distal end;
    an entrance at the distal end sized to receive the delivery catheter;
    a proximal end; and
    a hollow internal lumen with a longitudinal axis disposed between the proximal and distal ends,
    wherein the cleaning instrument is proximal to the hemostasis valve assembly.

8. The system of claim 1, further comprising a connecting port sized to receive an aspiration source.

9. The system of claim 1, wherein the hemostasis valve assembly further comprises:
    a central branch disposed between a first body cavity and second body cavity located proximal to the first;
    a seal disposed within the length of the central branch;
    a connecting port sharing a flow path with the first body cavity sized to receive an aspiration source; and
    a first connecting port sharing a flow path with the second body cavity sized to receive a fluid injection, and a second connecting port sharing a flow path with the second body cavity sized to receive an aspiration source.

10. The system of claim 1, wherein the nozzles are configured to provide varied incident angles of the sprayed fluid on the capture portion of the blood clot retrieval device.

11. The system of claim 10, wherein the incident angle ranges from nearly perpendicular to the retrieval path to a substantially more oblique angle.

* * * * *